(12) United States Patent
Mortimore et al.

(10) Patent No.: US 7,442,790 B2
(45) Date of Patent: Oct. 28, 2008

(54) CASPASE INHIBITORS AND USES THEREOF

(75) Inventors: Michael Mortimore, Burford (GB); Andrew Miller, Upton (GB); John Studley, Abingdon (GB); Jean-Damien Charrier, Wantage (GB)

(73) Assignee: Vertex Pharmaceuticals, Incorporated, Cambridge, MA (US)

( * ) Notice: Subject to any disclaimer, the term of this patent is extended or adjusted under 35 U.S.C. 154(b) by 0 days.

(21) Appl. No.: 11/770,093

(22) Filed: Jun. 28, 2007

(65) Prior Publication Data

US 2008/0015172 A1 Jan. 17, 2008

Related U.S. Application Data

(62) Division of application No. 10/153,971, filed on May 23, 2002, now Pat. No. 7,351,702.

(60) Provisional application No. 60/292,969, filed on May 23, 2001.

(51) Int. Cl.
*C07J 43/00* (2006.01)
(52) U.S. Cl. .................. 540/113; 540/587; 544/33; 544/35; 544/102; 544/347; 546/87; 546/104; 546/108; 548/441; 548/453; 548/492
(58) Field of Classification Search .......... 540/113, 540/587; 544/33, 35, 102, 347; 546/87, 546/104, 108; 548/441, 453, 492
See application file for complete search history.

(56) References Cited

U.S. PATENT DOCUMENTS 6,800,619 B2 * 10/2004 Charrier et al. ............. 514/183
2003/0232846 A1 12/2003 Golec et al.

FOREIGN PATENT DOCUMENTS

WO 98/16502 A1 4/1998
WO 99/56765 A1 11/1999
WO 01/72707 A2 10/2001

\* cited by examiner

*Primary Examiner*—Joseph McKane
*Assistant Examiner*—Chukwuma O Nwaonicha
(74) *Attorney, Agent, or Firm*—Jennifer G. Che

(57) ABSTRACT

This invention provides caspase inhibitors of formula I:

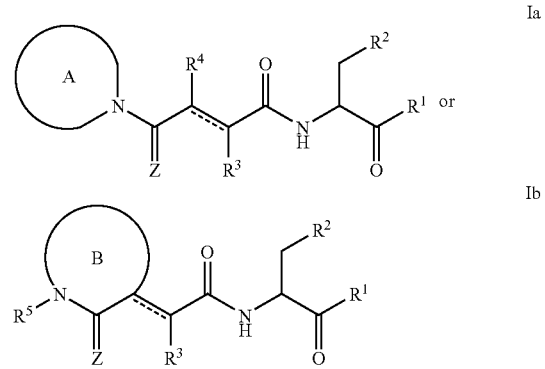

wherein Z is oxygen or sulfur; $R^1$ is hydrogen, $-CHN_2$, R, $CH_2OR$, $CH_2SR$, or $-CH_2Y$; ----between $R^3$ and $R^4$ represents a single or double bond; Y is an electronegative leaving group; $R^2$ is $CO_2H$, $CH_2CO_2H$, or esters, amides or isosteres thereof; $R^3$ is a group capable of fitting into the S2 subsite of a caspase enzyme; $R^4$ is a hydrogen or $C_{1-6}$ alkyl or $R^3$ and $R^4$ taken together form a ring; Ring A and Ring B are each heterocyclic rings, and R and $R^5$ are as described in the specification. The compounds are effective inhibitors of apoptosis and IL-1β secretion.

8 Claims, No Drawings

CASPASE INHIBITORS AND USES THEREOF

CROSS-REFERENCE TO RELATED APPLICATIONS

This application is a divisional of U.S. patent application Ser. No. 10/153,971, filed May 23, 2002, now U.S. Pat. No. 7,351,702; which claims the benefit of U.S. Provisional Application 60/292,969, filed May 23, 2001, the contents of which are incorporated herein by reference.

FILED OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283-1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

A four amino acid sequence primarily recognized by the caspases has been determined for enzyme substrates. Talanian et al., *J. Biol. Chem.* 272, 9677-9682, (1997); Thornberry et al., *J. Biol. Chem.* 272, 17907-17911, (1997). Knowledge of the four amino acid sequence primarily recognized by the caspases has been used to design caspase inhibitors. Reversible tetrapeptide inhibitors have been prepared having the structure $CH_3CO-[P4]-[P3]-[P2]-CH(R)CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); Nicholson et al., *Nature* 376, 37-43 (1995). Irreversible inhibitors based on the analogous tetrapeptide recognition sequence have been prepared where R is an acyloxymethylketone $-COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563-564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation*, 97, 276 (1998); Endres et al., *J Cerebral Blood Flow and Metabolism*, 18, 238, (1998); Cheng et al., J. Clin. Invest., 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism.

Plattner and Norbeck, in *Drug Discovery Technologies,* Clark and Moos, Eds. (Ellis Horwood, Chichester, England, 1990).

There are reports of modified peptide inhibitors. WO 91/15577 and WO 93/05071 disclose peptide ICE inhibitors of the formula:

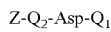

wherein Z is an N-terminal protecting group; Q2 is 0 to 4 amino acids; and $Q_1$ is an electronegative leaving group.

WO 99/18781 discloses dipeptide caspase inhibitors of the formula:

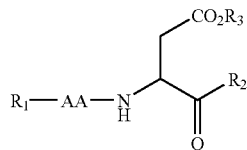

wherein $R_1$ is an N-terminal protecting group; AA is a residue of a natural α-amino acid or β-amino acid; $R_2$ is hydrogen or $CH_2R_4$ where $R_4$ is an electronegative leaving group; and $R_3$ is alkyl or hydrogen.

WO 99/47154 discloses dipeptide caspase inhibitors of the formula:

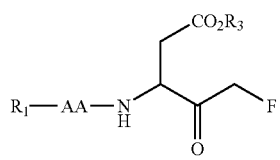

wherein $R_1$ is an N-terminal protecting group; AA is a residue of a non-natural α-amino acid or β-amino acid; and $R_2$ is optionally substituted alkyl or hydrogen.

WO 00/023421 discloses (substituted) acyl dipeptide apoptosis inhibitors having the formula:

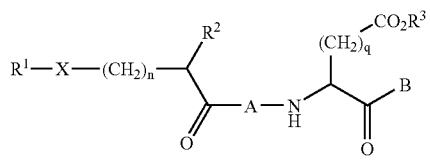

where n is 0, 1, or 2; q is 1 or 2; A is a residue of certain natural or non-natural amino acid; B is a hydrogen atom, a deuterium atom, $C_{1-10}$ straight chain or branched alkyl, cycloalkyl, phenyl, substituted phentyl, naphthyl, substituted naphthyl, 2-benzoxazolyl, substituted 2-oxazolyl, $(CH_2)_m$cycloalkyl, $(CH_2)_m$phenyl, $(CH_2)_m$(substituted phenyl), $(CH_2)_m$(1- or 2-naphthyl), $(CH_2)_m$heteroaryl, halomethyl, $CO_2R^{13}$, $CONR^{14}R^{15}$, $CH_2ZR^{16}$, $CH_2OCOaryl$, $CH_2OCO$(substituted aryl), $CH_2OCO$(heteroaryl), $CH_2OCO$(substituted heteroaryl), or $CH_2OPO(R^{17})R^{18}$, where $R^{13}$, $R^{14}$, $R^{15}$, $R^{16}$, $R^{17}$ and $R^{18}$ are defined in the application; $R^2$ is selected from a group containing hydrogen, alkyl, cycloalkyl, phenyl, substituted phenyl, $(CH_2)_mNH_2$; $R^3$ is hydrogen, alkyl, cycloalkyl, (cycloalkyl)alkyl, phenylalkyl, or substituted phenylalkyl; X is $CH_2$, C=O, O, S, NH, C=ONH or $CH_2OCONH$; and Z is an oxygen or a sulfur atom.

WO 97/24339 discloses inhibitors of interleukin-1β converter enzyme of the formula:

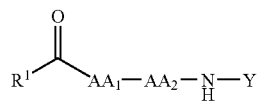

wherein $R^1$ represents H, alkyl, alkoxy, a carbocycle, a heterocycle, and various other groups; $AA^1$ and $AA^2$ are single bonds or amino acids; and Y represents a group of formula:

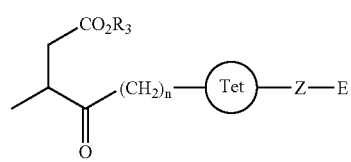

wherein the Tet ring represents a tetrazole ring; and Z represents, inter alia, alkylene, alkenylene, O, S, SO, and $SO_2$.

EP 618223 discloses ICE inhibitors of the formula:

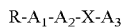

wherein R is H, a protecting group, or an optionally ring substituted $PhCH_2O$; $A_1$ is an α-hydroxy- or α-amino acid residue; $A_2$ is an α-hydroxyacid residue or α-amino acid or $A_1$ and $A_2$ form together a pseudodipeptide or a dipeptide mimetic residue; X is a residue derived from Asp wherein $A_3$ is $CH_2X_1COY_1$, $CH_2OY_2$, $CH_2SY_3$ or $CH_2(CO)_mY_6$ wherein $X_1$ is O or S, m is 0 or 1 and $Y_1, Y_2, Y_3$ and $Y_6$ are optionally substituted cyclic aliphatic or aryl groups.

WO 98/16502 discloses, inter alia, ICE inhibitors of the formula:

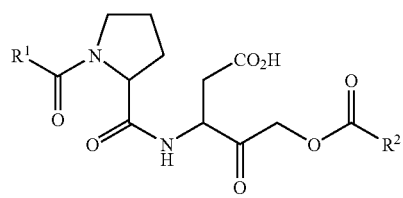

wherein $R_1$ and $R_2$ are as described in the application and the pyrrolidine ring is substituted by various groups.

WO 99/56765 discloses ICE inhibitors of the formula:

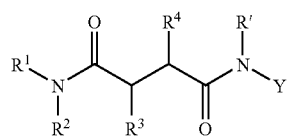

wherein R', $R^3$, $R^4$ and Y are described in the application and $R^1$ and $R^2$ are independently hydrogen, $C_1$-$C_6$ alkyl, OH, $(CH_2)_n$-substituted aryl, $(CH_2)_n$—O-aryl, $(CH_2)_n$—O-substituted aryl, $(CH_2)_n$—S-aryl, $(CH_2)_n$—S-substituted aryl, $(CH_2)_n$—S-heteroaryl, $(CH_2)_n$—S-substituted heteroaryl, $(CH_2)_n$—NR'-aryl, $(CH_2)_n$—NR'-substituted aryl, $(CH_2)_n$—

NR'-heteroaryl, (CH$_2$)$_n$—NR'-substituted heteroaryl, (CH$_2$)$_n$-heteroaryl, (CH$_2$)$_n$-substituted heteroaryl, each n is independently 0-6.

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are effective as inhibitors of caspases and cellular apoptosis. These compounds have the general formula I:

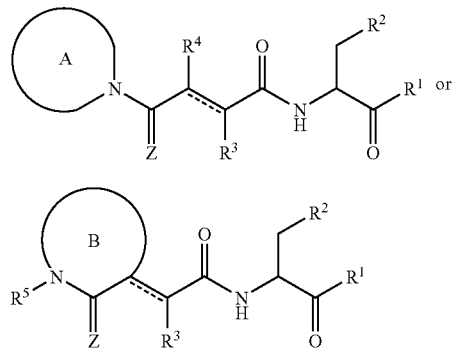

wherein:
- - - - between R$^3$ and R$^4$ represents a single or double bond;
Z is oxygen or sulfur;
R$^1$ is hydrogen, —CHN$_2$, —R, —CH$_2$OR, —CH$_2$SR, or —CH$_2$Y;
R is a C$_{1-12}$ aliphatic, aryl, aralkyl, heterocyclyl, or heterocylylalkyl;
Y is an electronegative leaving group;
R$^2$ is CO$_2$H, CH$_2$CO$_2$H, or esters, amides or isosteres thereof;
R$^3$ is a group capable of fitting into the S2 sub-site of a caspase;
R$^4$ is hydrogen or a C$_{1-6}$ aliphatic group that is optionally interrupted by —O—, —S—, —SO$_2$—, —CO—, —NH—, or —N(C$_{1-4}$ alkyl)-, or R$^3$ and R$^4$ taken together with their intervening atoms optionally form a 3-7 membered ring having 0-2 heteroatoms selected from nitrogen, oxygen or sulfur;
Ring A is a nitrogen-containing mono-, bi- or tricyclic ring system having 0-5 additional ring heteroatoms selected from nitrogen, oxygen or sulfur;
Ring B is a nitrogen-containing 5-7 membered ring having 0-2 additional ring heteroatoms selected from nitrogen, oxygen or sulfur;
R$^5$ is R$^6$, (CH$_2$)$_n$R$^6$, COR$^6$, CO$_2$R$^6$, SO$_2$R$^6$, CON(R$^6$)$_2$, or SO$_2$N(R$^6$)$_2$;
n is one to three; and
each R$^6$ is independently selected from hydrogen, an optionally substituted C$_{1-4}$ aliphatic group, an optionally substituted C$_{6-10}$ aryl group, or a mono- or bicyclic heteroaryl group having 5-10 ring atoms.

The compounds of this invention have inhibition properties across a range of caspase targets with good efficacy in cellular models of apoptosis. In addition, these compounds will have good cell penetration and pharmacokinetic properties and, as a consequence of their potency, have good efficacy against diseases where caspases are implicated.

DETAILED DESCRIPTION OF THE INVENTION

This invention provides novel compounds, and pharmaceutically acceptable derivatives thereof, that are useful as caspase inhibitors. The invention also provides methods for using the compounds to inhibit caspase activity and to treat caspase-mediated diseases. These compounds have the general formula I:

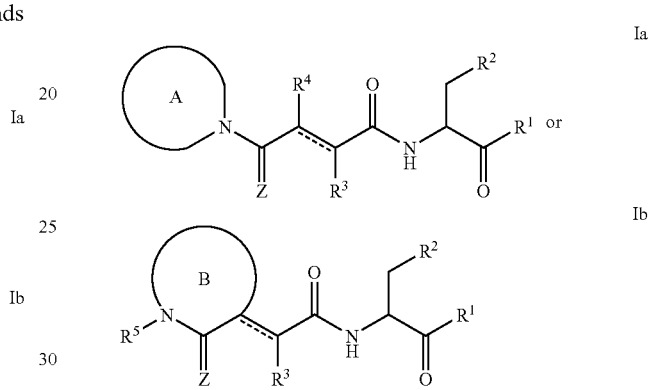

wherein:
- - - - between R$^3$ and R$^4$ represents a single or double bond;
Z is oxygen or sulfur;
R$^1$ is hydrogen, —CHN$_2$, —R, —CH$_2$OR, —CH$_2$SR, or —CH$_2$Y;
R is a C$_{1-12}$ aliphatic, aryl, aralkyl, heterocyclyl, or heterocylylalkyl;
Y is an electronegative leaving group;
R$^2$ is CO$_2$H, CH$_2$CO$_2$H, or esters, amides or isosteres thereof;
R$^3$ is a group capable of fitting into the S2 sub-site of a caspase;
R$^4$ is hydrogen or a C$_{1-6}$ aliphatic group that is optionally interrupted by —O—, —S—, —SO$_2$—, —CO—, —NH—, or —N(C$_{1-4}$ alkyl)-, or R$^3$ and R$^4$ taken together with their intervening atoms optionally form a 3-7 membered ring having 0-2 heteroatoms selected from nitrogen, oxygen or sulfur;
Ring A is a nitrogen-containing mono-, bi- or tricyclic ring system having 0-5 additional ring heteroatoms selected from nitrogen, oxygen or sulfur;
Ring B is a nitrogen-containing 5-7 membered ring having 0-2 additional ring heteroatoms selected from nitrogen, oxygen or sulfur;
R$^5$ is R$^6$, (CH$_2$)$_n$R$^6$, COR$^6$, CO$_2$R$^6$, SO$_2$R$^6$, CON(R$^6$)$_2$, or SO$_2$N(R$^6$)$_2$;
n is one to three; and
each R$^6$ is independently selected from hydrogen, an optionally substituted C$_{1-4}$ aliphatic group, an optionally substituted C$_{6-10}$ aryl group, or a mono- or bicyclic heteroaryl group having 5-10 ring atoms.

As used herein, the following definitions shall apply unless otherwise indicated. The term "aliphatic" as used herein means straight chained or branched C$_1$-C$_{12}$ hydrocarbons which are completely saturated or which contain one or more units of unsaturation. Aliphatic groups include substituted or unsubstituted linear, branched or cyclic alkyl, alkenyl, or alkynyl groups and hybrids thereof such as (cycloalkyl)alkyl, (cycloalkenyl)alkyl or (cycloalkyl)alkenyl. The term "alkyl" used alone or as part of a larger moiety refers to both straight and branched chains containing one to twelve carbon atoms. When the term alkyl is used as part of a larger moiety, as in aralkyl or heteroaralkyl, the alkyl portion will preferably contain one to six carbons.

The term "halogen" means F, Cl, Br, or I. The term "aryl" refers to monocyclic or polycyclic aromatic ring groups having five to fourteen atoms, such as phenyl, naphthyl and anthryl.

The term "heterocyclic group" refers to saturated and unsaturated monocyclic or polycyclic ring systems containing one or more heteroatoms and a ring size of three to nine such as furanyl, thienyl, pyrrolyl, pyrrolinyl, pyrrolidinyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholinyl, dithianyl, thiomorpholinyl, pyridazinyl, pyrimidinyl, pyrazinyl, piperazinyl, triazinyl, trithianyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, quinuclidinyl, carbazolyl, acridinyl, phenazinyl, phenothiazinyl, or phenoxazinyl. "Heteroaryl" refers to a heterocyclic ring that is aromatic. It is understood that the compounds of this invention are limited to those that can exist in nature as stable chemical compounds.

The term "carbocyclic group" refers to saturated monocyclic or polycyclic carbon ring systems of three to fourteen carbons which may be fused to aryl or heterocyclic groups. Examples include cyclohexyl, cyclopentyl, cyclobutyl, cyclopropyl, indanyl, tetrahydronaphthyl and the like.

The terms aliphatic, alkyl, aryl, heteroaryl, heterocyclyl, or carbocyclyl, used alone or as part of a larger moiety, refers to substituted or unsubstituted groups. When substituted, these groups may contain one or more substituents. Examples of suitable substituents include halogen, —R, —OR, —OH, —SH, —SR, protected OH (such as acyloxy), phenyl (Ph), substituted Ph, —OPh, substituted —OPh, —$NO_2$, —CN, —$NH_2$, —NHR, —$N(R)_2$, —NHCOR, —NHCONHR, —NHCON$(R)_2$, —NRCOR, —NHCO$_2$R, —CO$_2$R, —CO$_2$H, —COR, —CONHR, —CON$(R)_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is an aliphatic group or a substituted aliphatic group preferably having one to six carbons, more preferably having one to four carbons.

A substitutable nitrogen on a heterocyclic ring may be optionally substituted. Suitable substituents on the nitrogen include R, COR, S(O)$_2$R, and CO$_2$R, where R is an aliphatic group or a substituted aliphatic group preferably having one to six carbons, more preferably having one to four carbons.

Nitrogen and sulfur may be in their oxidized form, and nitrogen may be in a quaternized form.

The term "electronegative leaving group" has the definition known to those skilled in the art (see March, *Advanced Organic Chemistry*, 4$^{th}$ Edition, John Wiley & Sons, 1992). Examples of electronegative leaving groups include halogens such as F, Cl, Br, I, aryl, and alkylsulfonyloxy groups, trifluoromethanesulfonyloxy, OR, SR, —OC=O(R), —OPO$(R^7)(R^8)$, where R is an aliphatic group, an aryl group, an aralkyl group, a heterocyclic group, or a heterocyclylalkyl group; and $R^7$ and $R^8$ are independently selected from R or OR.

When the $R^2$ group is in the form of an ester or amide, the present compounds undergo metabolic cleavage to the corresponding carboxylic acids, which are the active caspase inhibitors. Because they undergo metabolic cleavage, the precise nature of the ester or amide group is not critical to the working of this invention. The structure of the $R^2$ group may range from the relatively simple diethyl amide to a steroidal ester. Examples of esters of $R^2$ carboxylic acids include, but are not limited to, $C_{1-12}$ aliphatic, such as $C_{1-6}$ alkyl or $C_{3-10}$ cycloalkyl, aryl, such as phenyl, aralkyl, such as benzyl or phenethyl, heterocyclyl or heterocyclylalkyl. Examples of suitable $R^2$ heterocyclyl rings include, but are not limited to, 5-6 membered heterocyclic rings having one or two heteroatoms such as piperidinyl, piperazinyl, or morpholinyl.

Amides of $R^2$ carboxylic acids may be primary, secondary or tertiary. Suitable substituents on the amide nitrogen include, but are not limited to, one or more groups independently selected from the aliphatic, aryl, aralkyl, heterocyclyl or heterocyclylalkyl groups described above for the $R^2$ ester alcohol. Likewise, other prodrugs are included within the scope of this invention. See generally Bradley D. Anderson, "Prodrugs for Improved CNS Delivery" in Advanced Drug Delivery Reviews (1996), 19, 171-202.

Isosteres or bioisosteres of $R^2$ carboxylic acids, esters and amides result from the exchange of an atom or group of atoms to create a new compound with similar biological properties to the parent carboxylic acid or ester. The bioisosteric replacement may be physicochemically or topologically based. An example of an isosteric replacement for a carboxylic acid is CONHSO$_2$(alkyl) such as CONHSO$_2$Me.

$R^3$ may be any group capable of fitting into the S2 sub-site of a known caspase. Such groups are known from the many caspase inhibitors that have been reported (see WO91/15577, WO93/05071, WO99/18781, WO99/47154, WO00/023421, WO9724339, EP618223, WO9816502, all of which are described above). Furthermore, the structures of several of the caspase enzymes including their S-2 subsites are also known. References to the caspase structure include the following: Blanchard H, et al., *J. Mol. Biol.* 302(1), 9-16 (2000); Wei Y, et al., *Chem. Biol.* 7(6):423-32 (2000); Lee D, et al., *J Biol. Chem.* 275(21):16007-14 (2000); Blanchard H, et al., *Structure Fold Des.* 7(9):1125-33 (1999); Okamoto Y, et al, *Chem. Pharm. Bull.* (Tokyo) 47(1):11-21 (1999); Margolin N, et al, *J. Biol. Chem.* 272(11):7223-8 (1997); Walker N P, et al., *Cell* 78(2):343-52 (1994); and Wilson K P, et al., *Nature* 370(6487):270-5 (1994).

Whether a group will fit into the S-2 subsite will depend on the particular caspase that is being considered. The size of the subsite will range from the small S-2 subsite of caspase-3 which permits a group up to the size of a $C_4$ aliphatic group to a relatively large subsite which permits a group having a molecular weight up to about 140 Daltons, such as a naphthyl group. The size, along with the electronic nature, of the $R^3$ group will influence the caspase selectivity of the inhibitor. From the references provided above, one skilled in the art could readily ascertain whether a group is capable of fitting favorably into an S-2 subsite of a caspase, for example, by using standard molecular modeling programs such as Quanta or Macromodel.

Suitable $R^3$ groups include hydrogen, a side chain of a natural α-amino acid, or a substituted or unsubstituted group having a molecular weight up to about 140 Daltons selected from aliphatic, aryl, aralkyl, heterocyclyl, and heterocyclylalkyl groups. Examples of $R^3$ aliphatic groups include methyl, ethyl, propyl, isopropyl, cyclopropyl, butyl, isobutyl, sec-butyl, tert-butyl, cyclobutyl, pentyl, cyclopentyl, hexyl, and cyclohexyl. Examples of $R^3$ aryl groups include phenyl, indenyl and naphthyl. Examples of $R^3$ heterocyclic groups include pyrrolidinyl, pyrrolinyl, imidazolidinyl, imidazolinyl, pyrazolinyl, pyrazolidinyl, piperidinyl, morpholinyl, thiomorpholinyl, piperazinyl, homopiperidinyl, and quinuclidinyl. Examples of $R^3$ heteroaryl groups include furanyl, thienyl, pyrrolyl, oxazole, thiazolyl, imidazolyl, pyrazolyl, isoxazolyl, isothiazolyl, oxadiazolyl, furazanyl, triazolyl, thiadiazolyl, pyridinyl, pyridazinyl, pyrimidinyl, pyrazinyl, triazinyl, indolyl, isoindolyl, indolinyl, benzofuranyl, benzothiophene, indazolyl, benzimidazolyl, benzthiazolyl, purinyl, quinolinyl, isoquinolinyl, quinolizinyl, cinnolinyl, phthalazinyl, quinazolinyl, quinoxalinyl, naphthyridinyl, pteridinyl, chromanyl, and isochromanyl. Each group may contain one or more substituents, as described above.

Ring A is an optionally substituted nitrogen-containing mono-, bi- or tricyclic ring system having 0-5 additional ring heteroatoms selected from nitrogen, oxygen or sulfur, preferably having 0-3 additional ring heteroatoms. Such rings include substituted or unsubstituted indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, 5H-dibenzo[b,f]azepine, 10,11-dihydro-5H-dibenzo[b,f]azepine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine. Suitable substituents on Ring A include one or more groups independently selected from a halogen, —R, —OR, —OH, —SH, —SR, protected OH (such as acyloxy), phenyl (Ph), substituted Ph, —OPh, substituted —OPh, —NO$_2$, —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, or —NHS(O)$_2$R, where each R is independently selected from an aliphatic group or a substituted aliphatic group. The R groups preferably have one to six carbons, more preferably one to four carbons.

Compounds of this invention where $R^2$ is COOH are gamma-ketoacids, which may exist in solution as either the open form 1a or the cyclized hemiketal form 1a'. The representation herein of either isomeric form is meant to include the other. Similarly, cyclization may also occur where R2 is CH$_2$COOH, and such cyclized isomers are understood to be included when the ring open form is represented herein.

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of hydrogen by a deuterium or tritium, or the replacement of a carbon by a $^{13}$C— or $^{14}$C-enriched carbon are within the scope of this invention.

One embodiment of this invention relates to compounds of formula Ia. Another embodiment relates to compounds of formula Ib. It is preferred that Z is oxygen. It is also preferred that ----between $R^3$ and $R^4$ is a single bond. Having the single bond will provide stereoisomers if $R^3$ or $R^4$ are other than hydrogen. Preferred stereoisomers of the present compounds will have the following configuration:

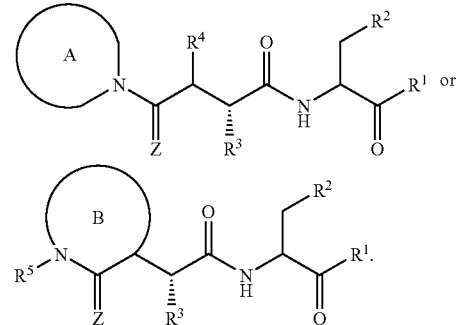

Another embodiment of this invention relates to compounds of formula Ia that have one or more, and preferably all, of the following features:

(i) $R^1$ is hydrogen, —R, —CH$_2$OR, —CH$_2$SR, or —CH$_2$Y. More preferably, $R^1$ is —CH$_2$OR, —CH$_2$SR, or —CH$_2$Y. An even more preferred $R^1$ is —CH$_2$Y. Most preferably, $R^1$ is —CH$_2$F.

(ii) $R^2$ is CO$_2$H or an ester, amide or isostere thereof.

(iii) $R^3$ is a group having a molecular weight up to about 140 Daltons, such as an aliphatic or aralkyl group. More preferably, $R^3$ is a $C_1$-$C_4$ alkyl group that will fit into the S2 subsite of a range of known caspases.

(iv) $R^4$ is hydrogen or $C_{1-6}$ alkyl, or $R^3$ and $R^4$ taken together form a ring of 5-7 ring atoms having 0-2 heteroatoms selected from nitrogen, oxygen or sulfur.

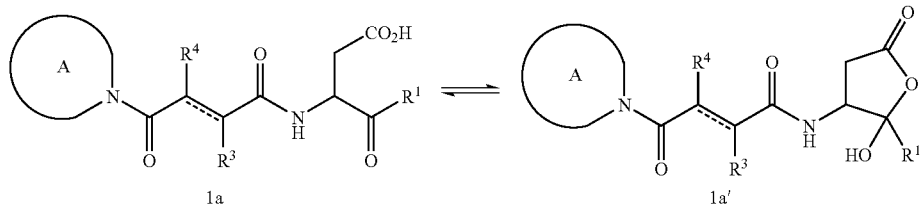

(v) Ring A is a monocyclic, bicyclic or tricyclic heterocyclic or heteroaryl ring system wherein each ring of the system has 5-7 ring atoms.

Ring A is a key feature of compounds of formula Ia. For the Ring A moiety, bicyclic or tricyclic heterocyclic or heteroaryl rings are preferred over monocyclic rings. Accordingly, a preferred embodiment relates to compounds having one or more, and preferably all, of the following features: (i) Z is oxygen; (ii) $R^1$ is —$CH_2OR$, —$CH_2SR$, or —$CH_2Y$, more preferably $R^1$ is —$CH_2Y$, and most preferably, $R^1$ is —$CH_2F$; (iii) $R^2$ is $CO_2H$ or an ester, amide or isostere thereof; (iv) $R^3$ is a group having a molecular weight up to about 140 Daltons, such as an aliphatic or aralkyl group, more preferably a $C_{1-4}$ alkyl group; and/or (v) Ring A is a bicyclic or tricyclic heterocyclic or heteroaryl ring system wherein each ring of the system has 5-7 ring atoms.

Examples of preferred monocyclic rings for Ring A include triazole, piperidine, morpholine, thiomorpholine, imidazole, pyrrolidine, pyrazole, and piperazine. Examples of preferred bicyclic rings for Ring A include indole, isoindole, indoline, indazole, benzimidazole, thieno[3,2-b]pyrrole, dihydroquinoxaline, dihydrocinnoline, dihydronaphthyridine, tetrahydronaphthyridine, tetrahydroquinoline, and tetrahydroisoquinoline, most preferably indole or indoline. Examples of preferred tricyclic rings for Ring A include carbazole, phenothiazine, β-carboline, pyrido[4,3-b]indole, 2,3,9-triazafluorene, 9-thia-2,10-diazaanthracene, 3,6,9-triazafluorene, phenoxazine, dibenzoazepine, dihydro-dibenzoazepine, dihydrophenazine, dihydroacridine, or dihydrophenanthridine, most preferably carbazole, phenothiazine or dihydrophenanthridine.

Specific examples of compounds I are shown in Table 1.

TABLE 1

Examples of Formula Ia compounds

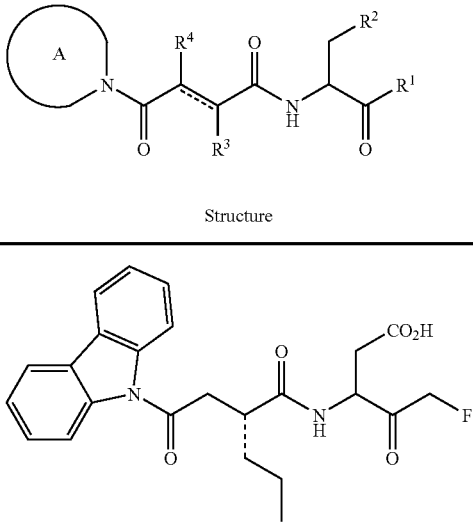

| No. | Structure |
| --- | --- |
| Ia-1 | 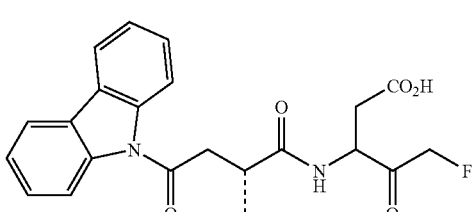 |
| Ia-2 | 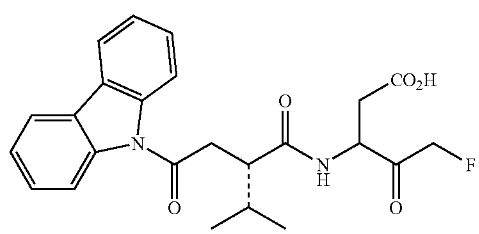 |
| Ia-3 | 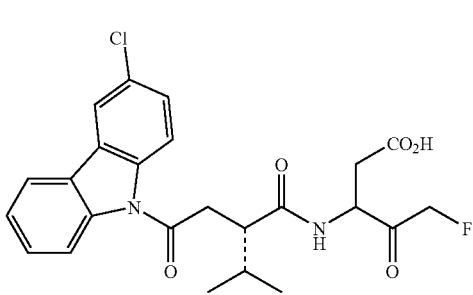 |

TABLE 1-continued
Examples of Formula Ia compounds
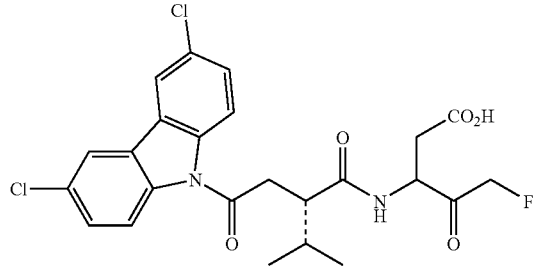
| No. | Structure |
| --- | --- |
| Ia-4 | 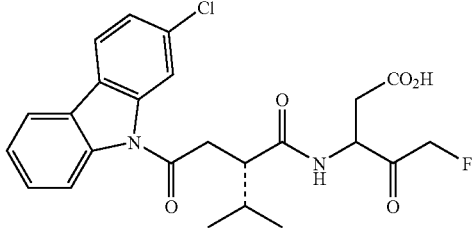 |
| Ia-5 | 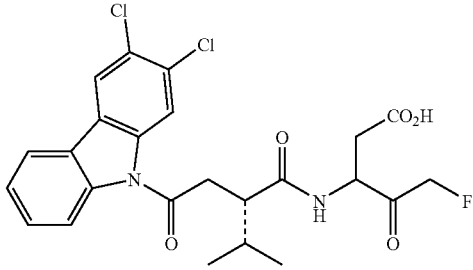 |
| Ia-6 | 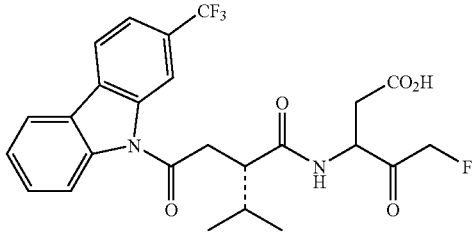 |
| Ia-7 | 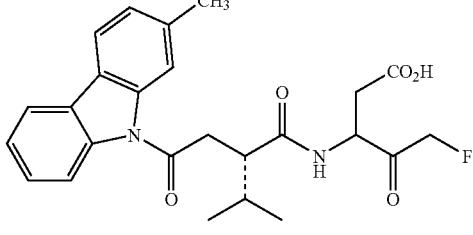 |
| Ia-8 | 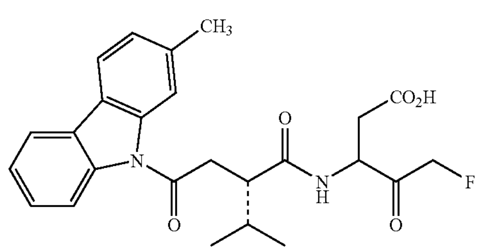 |

TABLE 1-continued

Examples of Formula Ia compounds

| No. | Structure |
|---|---|
| Ia-9 | |
| Ia-10 | |
| Ia-11 | |
| Ia-12 | |
| Ia-13 | |

TABLE 1-continued
Examples of Formula Ia compounds
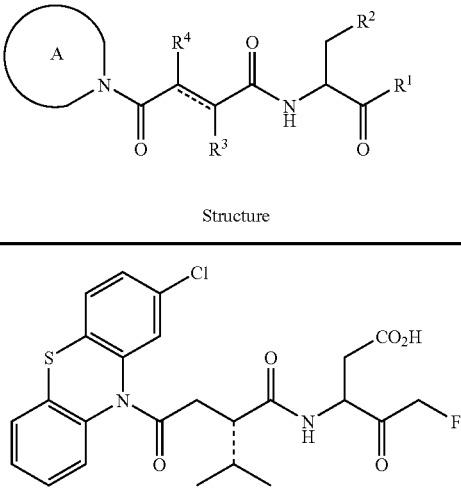
| No. | Structure |
|---|---|
| Ia-14 | 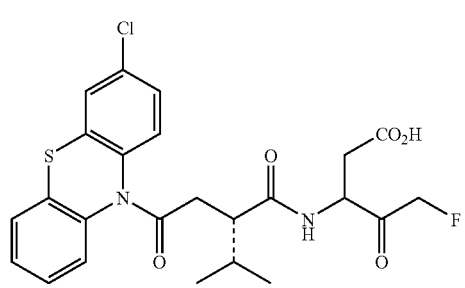 |
| Ia-15 | 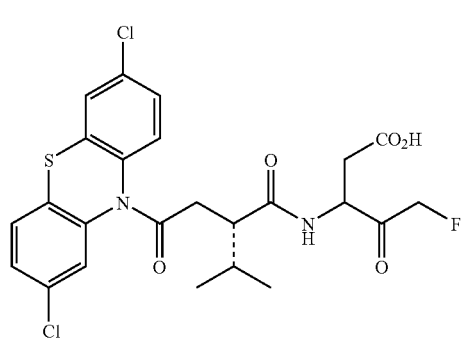 |
| Ia-16 | 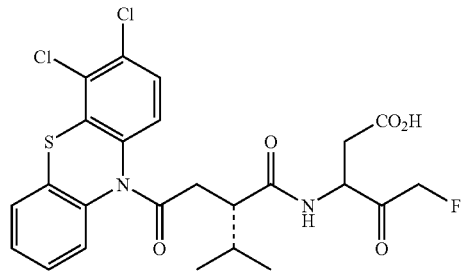 |
| Ia-17 | 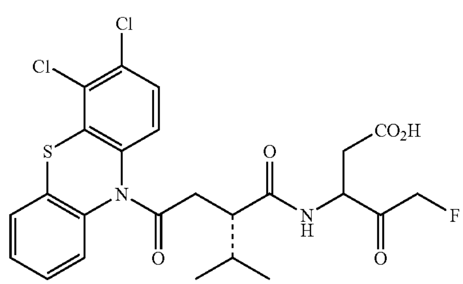 |

TABLE 1-continued

Examples of Formula Ia compounds

| No. | Structure |
|---|---|
| Ia-18 | 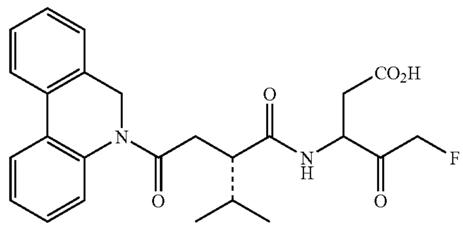 |
| Ia-19 | 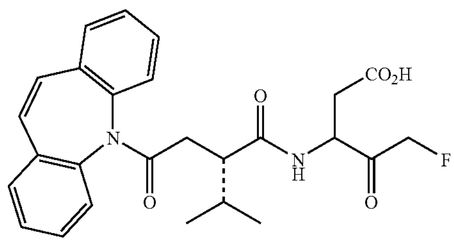 |
| Ia-20 | 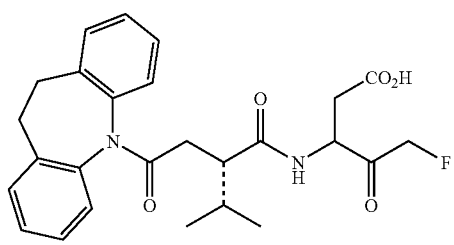 |
| Ia-21 | 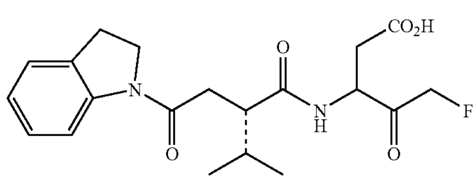 |
| Ia-22 | 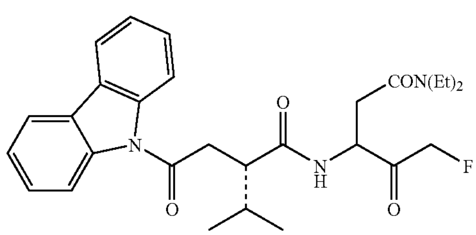 |

TABLE 1-continued

Examples of Formula Ia compounds

| No. | Structure |
|---|---|
| Ia-23 | 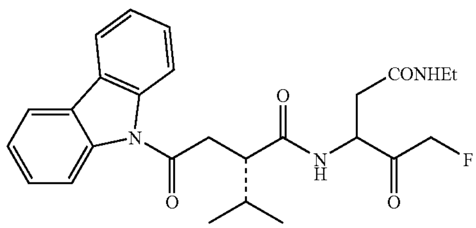 |
| Ia-24 | 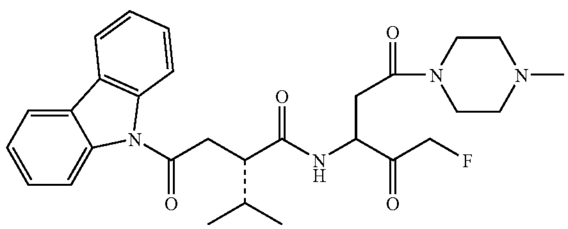 |
| Ia-25 | 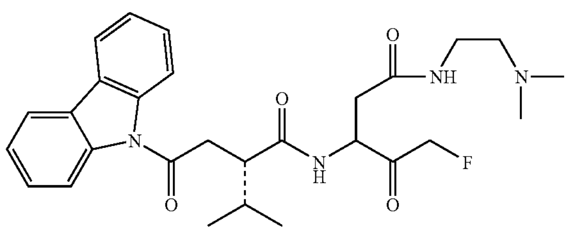 |
| Ia-26 | 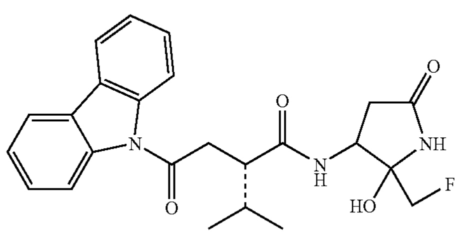 |
| Ia-27 | 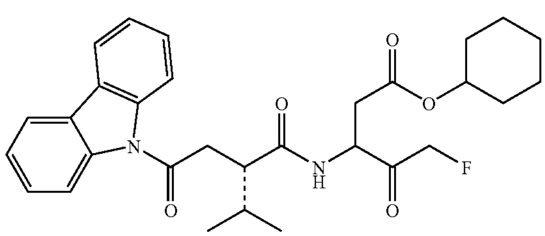 |

TABLE 1-continued

Examples of Formula Ia compounds

| No. | Structure |
|---|---|
| Ia-28 | (carbazole-N-CO-CH2-CH(iPr)-CO-NH-CH(CH2CO2Pr)-CO-CH2F) |
| Ia-29 | (carbazole-N-CO-CH2-CH(iPr)-CO-NH-CH(CH2CO2iPr)-CO-CH2F) |
| Ia-30 | (carbazole-N-CO-CH2-CH(iPr)-CO-NH-CH(CH2CO2CH3)-CO-CH2F) |
| Ia-31 | (carbazole-N-CO-CH2-CH(iPr)-CO-NH-CH(CH2CO2-cholesteryl)-CO-CH2F) |
| Ia-32 | (β-carboline-N-CO-CH2-CH(iPr)-CO-NH-CH(CH2CO2H)-CO-CH2F) |

TABLE 1-continued
Examples of Formula Ia compounds
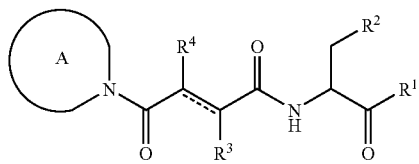
| No. | Structure |
|---|---|
| Ia-33 | 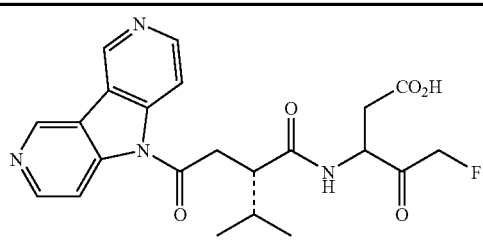 |
| Ia-34 | 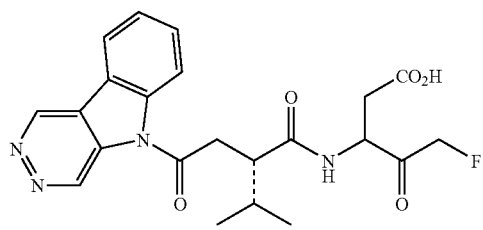 |
| Ia-35 | 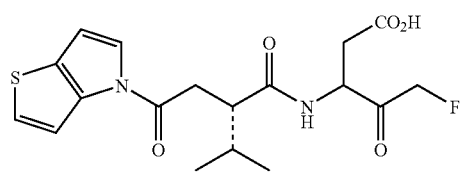 |
| Ia-36 | 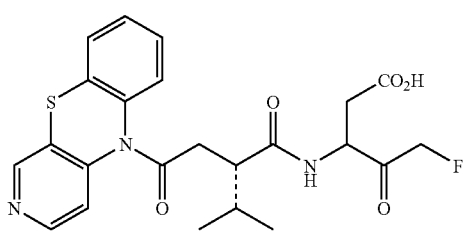 |
| Ia-37 | 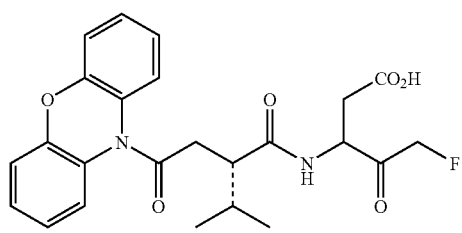 |
| Ia-38 | 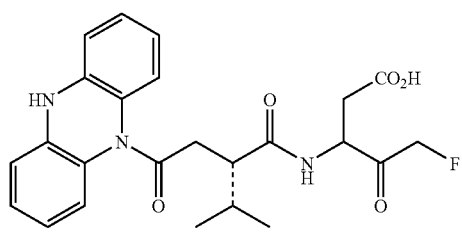 |

TABLE 1-continued
Examples of Formula Ia compounds
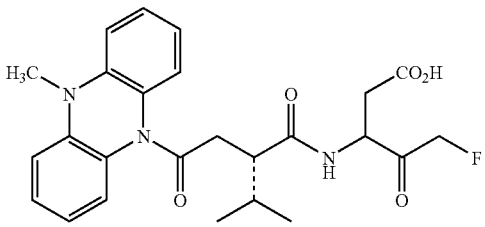
| No. | Structure |
|---|---|
| Ia-39 | 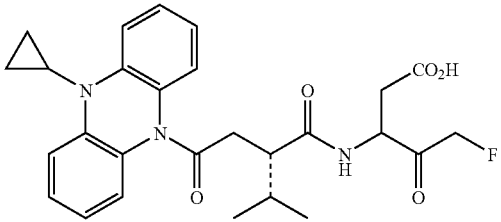 |
| Ia-40 | 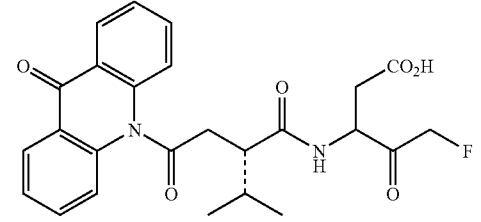 |
| Ia-41 | 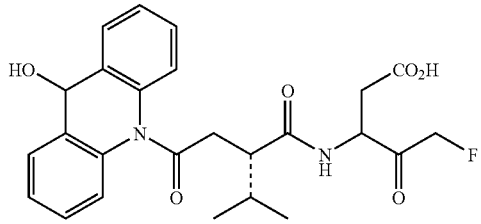 |
| Ia-42 | 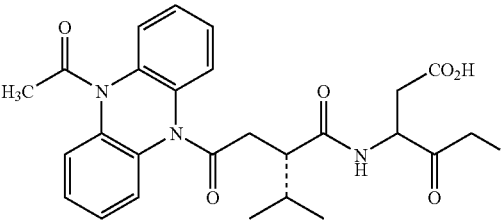 |
| Ia-43 | 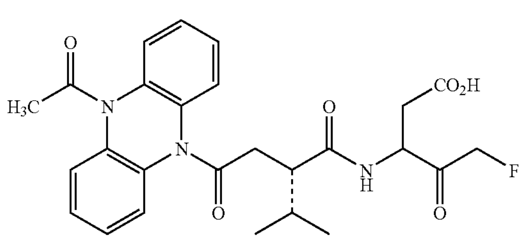 |

TABLE 1-continued

Examples of Formula Ia compounds

| No. | Structure |
|---|---|
| Ia-44 | 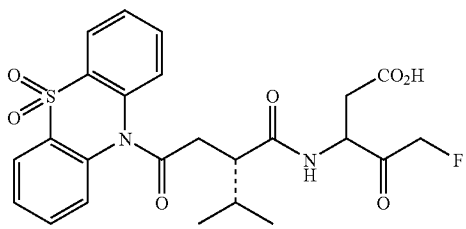 |

---

A preferred embodiment of this invention relates to compounds of formula Ia where Ring A is a tricyclic ring system having 1-6 heteroatoms, preferably 1-4 heteroatoms, selected from nitrogen, oxygen or sulfur wherein the end rings of the ring system have 5-7 ring atoms and the middle ring has 5 or 6 ring atoms. One aspect of this embodiment relates to compounds of formula II:

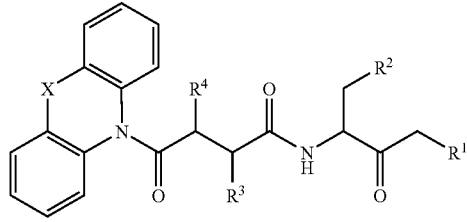

II where X is a bond, —S—, —O—, —CH$_2$—, or —NH—, and R$^1$, R$^2$, R$^3$ and R$^4$ are as described above. Where X is —CH$_2$—, each of the methylene hydrogens may be optionally and independently replaced by —OR, —OH, —SR, protected OH (such as acyloxy), —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is a C$_{1-4}$ aliphatic group. Where X is —NH—, the NH hydrogen may be replaced by alkyl, CO(alkyl), CO$_2$(alkyl), or SO$_2$(alkyl). Preferred groups for R$^1$, R$^2$ and R$^3$ are as described above.

Another embodiment of this invention relates to compounds of formula Ib that have one or more, and preferably all, of the following features:

(i) R$^1$ is hydrogen, —R, —CH$_2$OR, —CH$_2$SR, or —CH$_2$Y. More preferably, R$^1$ is —CH$_2$OR, —CH$_2$SR, or —CH$_2$Y. An even more preferred R$^1$ is —CH$_2$Y. Most preferably, R$^1$ is —CH$_2$F.

(ii) R$^2$ is CO$_2$H or an ester, amide or isostere thereof.

(iii) R$^3$ is a group having a molecular weight up to about 140 Daltons, such as an aliphatic or aralkyl group. More preferably, R$^3$ is a C$_1$-C$_4$ alkyl group that fits into the S2 subsite of a range of caspases.

(iv) Ring B is a nitrogen-containing five to seven membered ring having 0-1 additional ring heteroatoms selected from nitrogen, oxygen or sulfur.

(v) R$^5$ is an optionally substituted C$_{1-6}$ aliphatic group, an optionally substituted phenyl or an optionally substituted benzyl group.

Examples of specific formula Ib compounds are shown below in Table 2.

TABLE 2

Examples of Compounds of Formula Ib

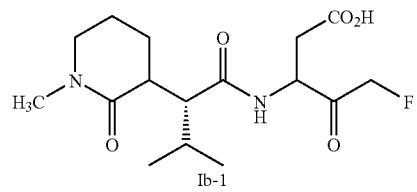

Ib-1

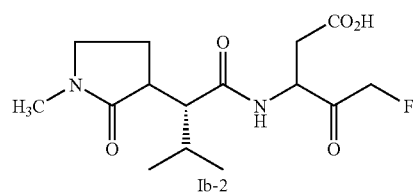

Ib-2

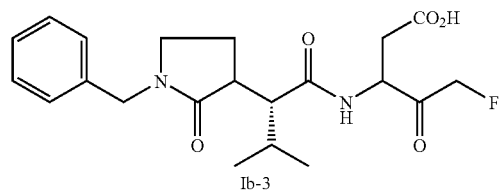

Ib-3

TABLE 2-continued

Examples of Compounds of Formula Ib

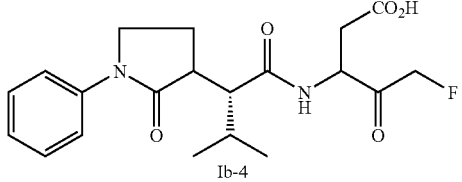

Ib-4

The compounds of this invention may be prepared in general by methods known to those skilled in the art for analogous compounds, as illustrated by the general scheme below and by the preparative examples that follow.

Scheme I

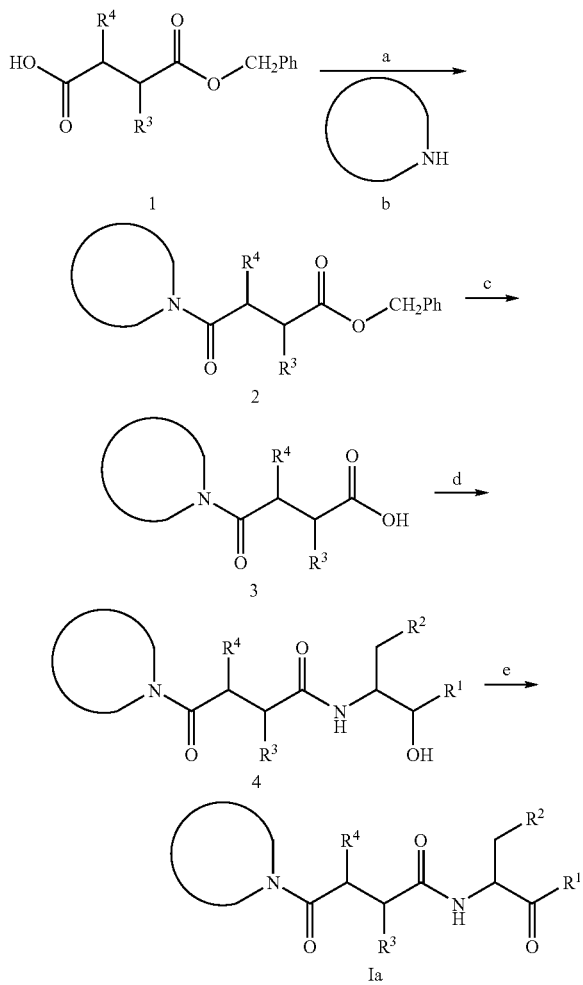

Reagents: (a) (COCl)$_2$/CH$_2$Cl$_2$; (b) Ring A; (c) H$_2$, Pd/C; (d) EDC, DMAP, HOBt, R$^2$CH$_2$CH(NH$_2$)CH(OH)R$^1$; (e) (i) Dess-Martin periodinane, (ii) TFA/DCM Scheme I above shows a synthetic route for obtaining compounds of formula Ia. Starting compound 1 may be obtained by a variety of general methods known in the art for substituted succinic acid derivatives. For asymmetric approaches to obtain the desired stereochemistry at the chiral centers bearing the R$^3$ and R$^4$ groups, see "Stereoselective Alkylation Reactions of Chiral Metal Enolates" Evans, D. A., in *Asymmetric Synthesis*, Vol. 3, Chapter 1 pages 1-110; Morrison, J. D. Ed., Academic Press, New York, 1983. In steps (a) and (b) the acid chloride of 1 is formed and then coupled with Ring A as the free amine to provide the amide 2. Step (c) shows a hydrogenolysis of the benzyl ester to provide carboxylic acid 3. Alternatively, compound 3 may be obtained from other esters using appropriate de-esterification conditions. In step (d), 3 is coupled with an amino alcohol to provide the amide 4. Depending on the nature of R$^1$ and R$^2$ an amino ketone may be used, in place of the amino alcohol, which avoids the subsequent oxidation step. In the case of fluoromethyl ketones where R$^1$ is CH$_2$F, the corresponding amino alcohol may be obtained according to the method of Revesz et al., *Tetrahedron Lett.,* 1994, 35, 9693. Finally the hydroxyl group in compound 4 is oxidized and the resulting compound treated appropriately according to the nature of R$^2$. For example, if the product Ia requires R$^2$ to be a carboxylic acid, then R$^2$ in 4 is preferably an ester and the final step in the scheme is a hydrolysis.

The compounds of this invention are designed to inhibit caspases. Therefore, the compounds of this invention may be assayed for their ability to inhibit apoptosis, the release of IL-1β or caspase activity directly. Assays for each of the activities are described below in the Testing section and are also known in the art.

One embodiment of this invention relates to a composition comprising a compound of formula I or a pharmaceutically acceptable salt thereof, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia,epilepsy, myocardial ischemia, acute and chronic heart disease, myocardial infarction, congestive heart failure, atherosclerosis, coronary artery bypass graft, spinal muscular atrophy, amyotrophic lateral sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polyaptic kidney disease, H. pylori-associated gastric and duodenal ulcer disease, HIV infection, tuberculosis, and meningitis. The compounds and compositions are also useful in treating complications associated with coronary artery bypass grafts and as a component of immunotherapy for the treatment of various forms of cancer.

The caspase inhibitors of this invention are also useful in the preservation of cells, such as tissues and organs. The method of cell preservation comprises the step of bathing the cells in a solution of the compound or a pharmaceutically acceptable derivative thereof.

The amount of compound present in the above-described compositions should be sufficient to cause a detectable decrease in the severity of the disease or in caspase activity and/or cell apoptosis, as measured by any of the assays described in the examples.

The compounds of this invention are also useful in methods for preserving cells, such as may be needed for an organ transplant or for preserving blood products. Similar uses for caspase inhibitors have been reported (Schierle et al., *Nature Medicine*, 1999, 5, 97). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

SYNTHESIS EXAMPLES

The following Examples provide synthetic procedures for selected compounds of this invention.

Example 1

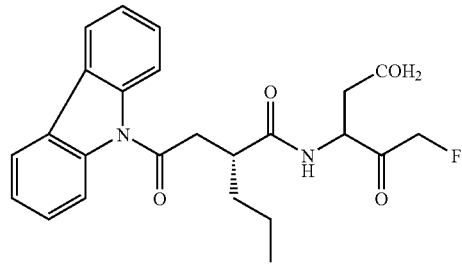

[3S/R(2S)]-3-[2-(Carbazol-9-yl-2-oxo-ethyl)-pentanoylamino]-5-fluoro-4-oxo-pentanoic acid Method A:
(4S)-Benzyl-3-pentanoyl-oxazolidin-2-one

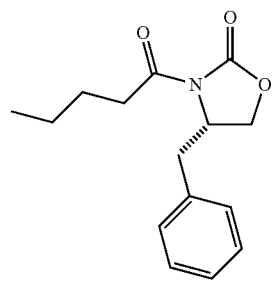

A solution of 4(S)-(−)-benzyl-2-oxazolidinone (10 g, 56.43 mmol) in anhydrous THF (200 ml) at −78° C. was treated with a 2.5M solution of n-butyl lithium in hexanes (23.70 ml, 59.26 mmol) with stirring. The reaction mixture was allowed to stir at −78° C. for 30 min before valeryl chloride (7.57 ml, 62.10 mmol) was added. The reaction mixture was then allowed to warm to ambient temperature over 15 h after which it was diluted with $NH_4Cl$ solution, diluted with ethyl acetate and washed with brine. The organic phase was dried ($Na_2SO_4$) and concentrated to give a gum. This was purified by flash chromatography (10% EtOAc in 40/60 hexanes) to give the sub-title compound (14.61 g, 99%) as a colourless oil: $^1H$ NMR (400 MHz, $CDCl_3$) δ 0.94-1.20 (3H, m), 1.35-1.50 (2H, m), 1.62-1.80 (2H, m), 2.74-2.84 (1H, m), 2.86-3.08 (2H, m), 3.27-3.39 (1H, m), 4.11-4.26 (2H, m), 4.62-4.76 (1H, m), 7.18-7.40 (5H, m).

Method B: [4S(3R)]-3-(4-Benzyl-2-oxo-oxazolidine-3-carbonyl)-hexanoic acid tert-butyl ester

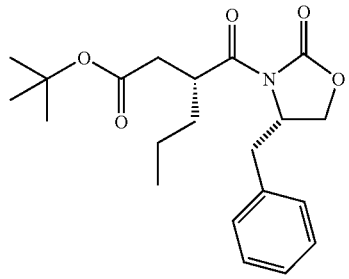

A solution of (4S)-benzyl-3-pentanoyl-oxazolidin-2-one (14.20 g, 54.34 mmol) in THF (100 mL) at −78° C. was treated over 10 min with a 1M solution of sodium bis(trimethylsilyl)amide in THF (59.80 ml, 59.77 mmol) with stirring. The reaction mixture was allowed to stir at −78° C. for 30 min before tert-butyl bromoacetate (10.43 ml, 70.64 mmol) was added. The reaction mixture was then allowed to stir for a further 3.5 h at −78° C. after which it was diluted with NH$_4$Cl solution, diluted with ethyl acetate and washed sequentially with NaHCO$_3$ solution and brine. The organic phase was dried (Na$_2$SO$_4$) and concentrated to give a gum. On standing a white solid formed and this was recrystallized from 40/60 DCM/hexanes to give the sub-title compound (14.62 g, 72%) as a white solid: $^1$H NMR (400 MHz, CDCl$_3$) δ 0.81-1.20 (3H, m), 1.21-1.76 (13H, m), 2.41-2.55 (1H, m), 2.66-2.92 (2H, m), 3.27-3.40 (1H, m), 4.05-4.26 (2H, m), 4.61-4.72 (1H, m), 7.12-7.40 (5H, m).

Method C: (2R)-2-Propyl-succinic acid 1-benzyl ester 4-tert-butyl ester

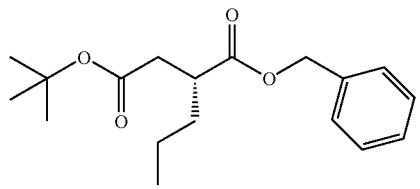

A solution of benzyl alcohol (4.62 ml, 44.64 mmol) in THF (80 ml) at −20° C. was treated with a 2.5M solution of n-butyl lithium in hexanes (13.36 ml, 33.48 mmol) with stirring. The reaction mixture was allowed to warm to −5° C. over 40 min before a solution of [4S(3R)]-3-(4-benzyl-2-oxo-oxazolidine-3-carbonyl)-hexanoic acid tert-butyl ester (8.38 g, 22.32 mmol) in THF (20 ml) was added. The reaction mixture was warmed to ambient temperature over 15 h after which it was diluted with NH$_4$Cl solution and ethyl acetate and washed with brine. The organic phase was dried (Na$_2$SO$_4$) and concentrated to give a gum. This was purified by flash chromatography (11% EtOAc in 40/60 hexanes) to give the sub-title compound (4.56 g, 67%) as a colourless oil: $^1$H NMR (400 MHz, CDCl$_3$) δ 0.83-1.00 (3H, m), 1.21-1.71 (13H, m), 2.34-2.45 (1H, m), 2.75-2.95 (1H, m), 5.09-5.25 (2H, m), 7.30-7.43 (5H, m).

Method D: (2R)-2-Propyl-succinic acid 1-benzyl ester

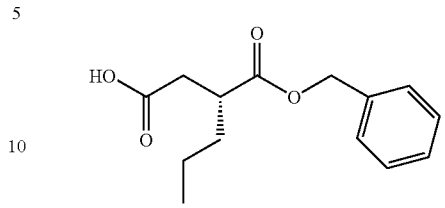

A stirred solution of (2R)-2-propyl-succinic acid 1-benzyl ester 4-tert-butyl ester (4.56 g, 14.88 mmol) in anhydrous DCM (20 mL), at 0° C., was treated with a solution of trifluoroacetic acid (10 mL) in anhydrous DCM (10 mL). The reaction mixture was allowed to warm to ambient temperature over 3 h before being concentrated under reduced pressure. The residue was dissolved in dry DCM, before concentrating again. This process was repeated several times in order to remove excess trifluoroacetic acid to leave the sub-title compound (3.70 g, 99%) as a gum: $^1$H NMR (400 MHz, CDCl$_3$) δ 0.82-0.99 (3H, m), 1.21-1.76 (4H, m), 2.45-2.60 (1H, m), 2.76-3.00 (2H, m), 5.10-5.21 (2H, m), 7.28-7.43 (5H, m), 7.83-8.18 (1H, m).

Method E: (2R)-2-(2-Carbazol-9-yl-2-oxo-ethyl)-pentanoic acid benzyl ester

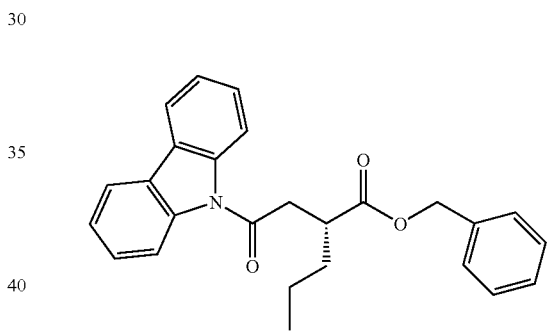

A stirred solution of carbazole (2.49 g, 14.88 mmol) in anhydrous THF (30 mL), at −78° C., was treated with a 1.0M solution of lithium bis(trimethylsilyl)amide in THF (14.88 ml, 14.88 mmol). The reaction mixture was allowed to warm to ambient temperature over 2 h before being re-cooled to −78° C.

A solution of (2R)-2-Propyl-succinic acid 1-benzyl ester (3.70 g, 14.78 mmol) in anhydrous DCM (20 mL), stirring at 0° C., was treated with oxalyl chloride (1.43 ml, 16.37 mmol) and DMF (14 drops). The reaction mixture was stirred at 0° C. for 1 h before being concentrated in vacuo. The residue was dissolved in anhydrous THF (10 ml) and added to the lithium anion of carbazole previously prepared, at −78° C. The reaction mixture was warmed to ambient temperature over 40 h after which it was diluted with NH$_4$Cl solution, and ethyl acetate and washed sequentially with 2N HCl, NaHCO$_3$ solution and brine. The organic phase was dried (Na$_2$SO$_4$) and concentrated to give a gum which was purified by flash chromatography (10% EtOAc in 40/60 hexanes) to give the sub-title compound (4.50 g, 76%) as a semi solid/oil which also contained carbazole: $^1$H NMR (400 MHz, CDCl$_3$) δ 0.82-1.05 (3H, m), 1.11-1.99 (4H, m), 3.18-3.38 (2H, m), 3.56-3.71 (1H, m), 5.10-5.30 (2H, m), 7.11-7.60 (9H, m), 7.92-8.29 (4H, m)

Method F: (2R)-2-(2-Carbazol-9-yl-2-oxo-ethyl)-pentanoic acid

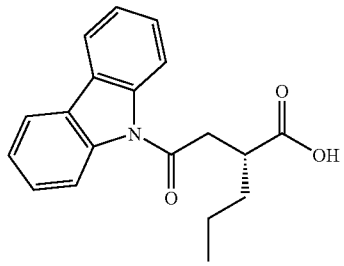

A stirred solution of (2R)-2-(2-Carbazol-9-yl-2-oxo-ethyl)-pentanoic acid benzyl ester (4.50 g, 11.26 mmol) in EtOAc (60 mL) was treated with 10% Pd on carbon (~400 mg) and the reaction mixture then placed under an atmosphere of hydrogen. After 1 h further 10% Pd on carbon (~300 mg) was added and the reaction mixture was placed under hydrogen, with stirring, for a further 3 h after which the reaction mixture was filtered through a celite pad and concentrated to give the sub-title compound (2.94 g, 84%) as a white solid which also contained carbazole: $^1$H NMR (400 MHz, CDCl$_3$) δ 0.92-1.04 (3H, m), 1.32-2.00 (4H, m), 3.19-3.34 (2H, m), 3.58-3.70 (1H, m), 7.30-7.53 (4H, m), 8.00-8.30 (4H, m).

Method G: [3S/R, 4S/R, (2R)]-3-[2-(2-Carbazol-9-yl-2-oxo-ethyl)-pentanoylamino]-5-fluoro-4-hydroxy-pentanoic acid tert-butyl ester

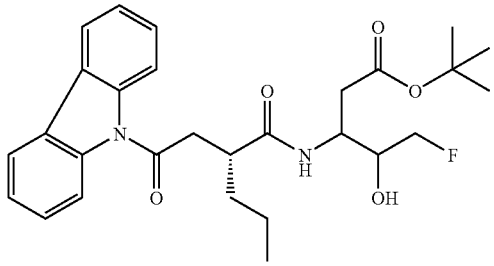

A stirred mixture of (2R)-2-(2-carbazol-9-yl-2-oxo-ethyl)-pentanoic acid (2.94 g, 9.50 mmol), 3-amino-5-fluoro-4-hydroxy-pentanoic acid tert-butyl ester (2.07 g, 9.99 mmol), HOBT (1.41 g, 10.43 mmol), DMAP (1.34 g, 10.97 mmol) and anhydrous THF (40 mL) was cooled to 0° C. then EDC (2.00 g, 10.43 mmol) was added. The mixture was allowed to warm to room temperature during 16 h then concentrated under reduced pressure. The residue purified by flash chromatography (33% EtOAc in 40/60 hexanes) to give the sub-title compound (2.51 g, 53%) as a foam: $^1$H NMR (400 MHz, CDCl$_3$) δ 0.90-1.03 (3H, m), 1.20-1.90 (13H, m), 2.50-3.00 (3H, m), 3.12-3.26 (1H, m), 3.59-3.80 (2H, m), 4.00-4.68 (3H, m), 6.53-6.89 (1H, m), 7.30-7.52 (4H, m), 7.95-8.05 (2H, m), 8.15-8.26 (2H, m); $^{19}$F NMR (376 MHz, CDCl$_3$) δ −229.10, −229.34, −230.95, −231.09.

Method H: [3S/R, (2R)]-3-[2-(2-Carbazol-9-yl-2-oxo-ethyl)-pentanoylamino]-5-fluoro-4-oxo-pentanoic acid tert-butyl ester

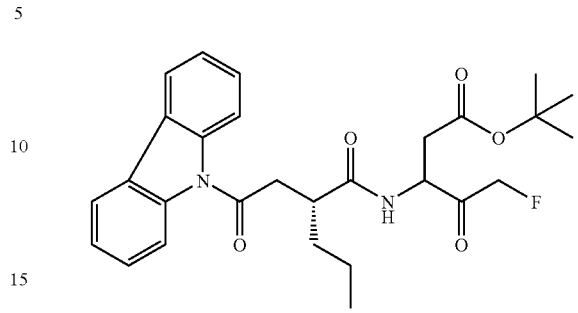

A stirred solution of [3S/R, 4S/R, (2R)]-3-[2-(2-carbazol-9-yl-2-oxo-ethyl)-pentanoylamino]-5-fluoro-4-hydroxy-pentanoic acid tert-butyl ester (2.51 g, 5.03 mmol) in anhydrous DCM (60 ml) was treated with 1,1,1-triacetoxy-1,1-dihydro-1,2-benziodoxol-3(1H)-one (2.35 g, 5.53 mmol) at 0° C. The resulting mixture was kept at 0° C. for 3 h, diluted with DCM, and then washed sequentially with saturated aqueous sodium thiosulphate, NaHCO3 solution and brine. The organics were dried (Na$_2$SO$_4$) and concentrated. The residue was purified by flash chromatography (25% ethyl acetate in 40/60 hexanes) to afford the sub-title compound as an off white solid (1.437 g, 57%): IR (solid) 1722, 1689, 1636, 1531, 1441, 1365, 1279, 1155 cm-1; $^1$H NMR (400 MHz, CDCl$_3$) δ 0.85-1.50 (3H, m), 1.35-1.54 (11H, m), 1.55-1.69 (1H, m), 1.78-1.95 (1H, m), 2.67-3.28 (4H, m), 3.60-3.79 (1H, m), 4.80-5.59 (3H, m), 6.89-7.04 (1H, m), 7.33-7.54 (4H, m), 7.98-8.04 (2H, m), 8.15-8.28 (2H, m); $^{13}$C (100 MHz, CDCl$_3$) δ 14.12, 14.40, 14.47, 14.60, 20.78, 20.84, 21.47, 28.32, 28.42, 28.48, 29.77, 33.63, 34.58, 34.91, 40.05, 43.05, 43.26, 43.29, 52.60, 53.00, 53.64, 66.90, 66.99, 82.62, 82.69, 85.53, 116.88, 116.94, 120.28, 120.31, 124.27, 127.76, 127.86, 128.69, 128.77, 128.99, 138.80, 171.21, 171.29, 172.21, 172.25, 175.53, 176.03, 203.04, 203.20, 203.30, 203.46; $^{19}$F (376 MHz, CDCl$_3$) δ −232.12, −233.24.

Method I: [3S/R, (2R)]-3-[2-(2-Carbazol-9-yl-2-oxo-ethyl)-pentanoylamino]-5-fluoro-4-oxo-pentanoic acid

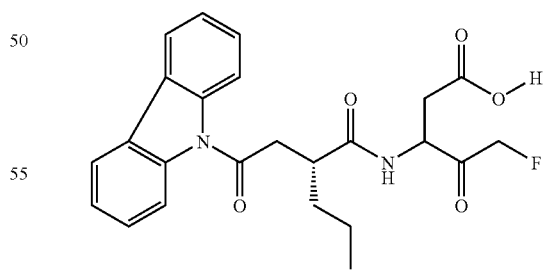

A solution of [3S/R, (2R)]-3-[2-(2-carbazol-9-yl-2-oxo-ethyl)-pentanoylamino]-5-fluoro-4-oxo-pentanoic acid tert-butyl ester (1.43 g, 2.88 mmol) in anhydrous DCM (20 ml) was treated with a solution of TFA (10 ml) in anhydrous DCM (10 ml) with stirring. The mixture was stirred at 0° C. for 2 h then at room temperature for 2 h. The mixture was concentrated under reduced pressure and then the residue was dissolved in dry DCM. This process was repeated several times in order to remove excess trifluoroacetic acid. The off-white solid was recrystallized from Et$_2$O/40/60 hexanes to give the title compound as a white powder (71 mg): IR (solid) 1746, 1689, 1641, 1541, 1436, 1374, 1284, 1207, 1160 cm-1; $^1$H NMR (400 MHz, d$_6$-DMSO) δ 0.80-1.00 (3H, m), 1.20-1.76 (4H, m), 2.30-2.90 (2H, m), 2.95-3.24 (1H, m), 3.26-3.59 (2H, m), 4.25-4.79 (1.5H, m), 5.02-5.43 (1.5H, m), 7.36-7.58 (4H, m), 8.10-8.30 (4H, m), 8.54-8.91 (1H, m); $^{13}$C NMR (100 MHz, DMSO) δ 14.31, 20.03, 20.13, 21.92, 22.51, 34.36, 34.77, 41.20, 41.62, 44.06, 51.77, 52.84, 83.45, 85.22, 116.70, 120.54, 123.91, 124.01, 127.85, 126.01, 138.20, 172.15, 172.36, 172.96, 173.00, 175.32, 175.48, 202.60, 203.10; $^{19}$F (376 MHz, DMSO) δ −226.68, −226.73, −231.21, −232.95, −233.38, −233.52.

Example 2

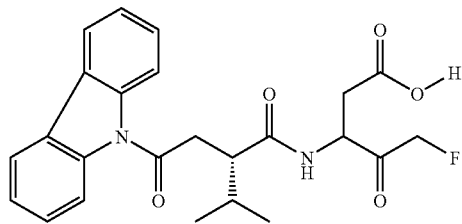

[3S/R(2S)]-3-[2-(2-Carbazol-9-yl-2-oxo-ethyl)-3-methyl-butyrylamino]-5-fluoro-4-oxo-pentanoic acid This was prepared using procedures similar to those described in Methods A-I. The product was isolated as a white powder (71% for final step): IR (solid) 1739, 1682, 1646, 1545, 1447, 1381, 1290, 1209, 1170 cm$^{-1}$; $^1$H NMR (400 MHz, DMSO+TFA) δ 0.79-1.08 (6H, m), 1.89-2.15 (1H, m), 2.31-3.60 (5H, m), 4.21-4.78 (1.25H, m), 4.98-5.45 (1.75H, m), 7.38-7.60 (4H, m), 8.14-8.35 (4H, m), 8.56-8.90 (1H, m); $^{13}$C NMR (100 MHz, DMSO) δ 20.46, 20.84, 21.04, 21.21, 30.77, 30.85, 33.37, 34.83, 35.24, 38.16, 38.89, 47.67, 48.23, 52.19, 53.43, 83.96, 84.01, 85.72, 85.77, 117.16, 121.02, 124.43, 126.42, 126.52, 128.42, 138.75, 172.64, 172.90, 173.85, 173.90, 174.74, 174.93, 175.16, 202.91, 203.04, 203.51, 203.65; $^{19}$F (376 MHz, DMSO) δ −226.63, −226.68, −231.24, −233.16, −233.38, −233.55.

TESTING METHODS

Enzyme Assays

The assays for caspase inhibition are based on the cleavage of a fluorogenic substrate by recombinant, purified human Caspases-1, -3, -7 or -8. The assays are run in essentially the same way as those reported by Garcia-Calvo et al. (J. Biol. Chem. 273 (1998), 32608-32613), using a substrate specific for each enzyme. The substrate for Caspase-1 is Acetyl-Tyr-Val-Ala-Asp-amino-4-methylcoumarin. The substrate for Caspases-3, -7 and -8 is Acetyl-Asp-Glu-Val-Asp-amino-4-methylcoumarin. The observed rate of enzyme inactivation at a particular inhibitor concentration, $k_{obs}$, is computed by direct fits of the data to the equation derived by Thornberry et al. (Biochemistry 33 (1994), 3943-3939) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression. Many of the present compounds that were tested showed the following activities: against caspase-1, $k_{inact}$ values between 25,000 and 1,500,000 M$^{-1}$s$^{-1}$; against caspase-3, $k_{inact}$ values between 9,000 and 1,500,000 M$^{-1}$s$^{-1}$; against caspase-8, $k_{inact}$ values between 10,000 and 700,000 M$^{-1}$s$^{-1}$.

Inhibition of IL-1β Secretion from Mixed Population of Peripheral Blood Mononuclear Cells (PBMC)

Processing of pre-IL-1β by caspase-1 may be measured in cell culture using a variety of cell sources. Human PBMC obtained from healthy donors provides a mixed population of lymphocyte and mononuclear cells that produce a spectrum of interleukins and cytokines in response to many classes of physiological stimulators.

Experimental Procedure

The test compound is dissolved in dimethyl sulfoxide (DMSO, Sigma #D-2650) to give a 100 mM stock solution. This is diluted in complete medium consisting of RPMI containing 10% heat inactivated FCS (Gibco BRL #10099-141), 2 mM L-Glutamine (Sigma, #G-7513), 100 U penicillin and 100 µg/ml streptomycin (Sigma #P-7539). The final concentration range of test compound is from 100 µM down to 6 nM over eight dilution steps. The highest concentration of test compound is equivalent to 0.1% DMSO in the assay.

Human PBMC are isolated from Buffy Coats obtained from the blood bank using centrifugation on Ficoll-Paque leukocyte separation medium (Amersham, #17-1440-02) and the cellular assay is performed in a sterile 96 well flat-bottomed plate (Nunc). Each well contains 100 µl of the cell suspension, 1×10$^5$ cells, 50 µl of compound dilutions and 50 µl of LPS (Sigma #L-3012) at 50 ng/ml final concentration. Controls consist of cells ±LPS stimulation and a serial dilution of DMSO diluted in the same way as compound. The plates are incubated for 16-18 h at 37° C. in 5% CO$_2$ & 95% humidity atmosphere.

After 16-18 h the supernatants are harvested after centrifuging the plates at 100×g at 18° C. for 15 min and assayed for their IL-1β content. Measurement of mature IL-1β in the supernatant is performed using the Quantikine kits (R&D Systems) according to manufacturer's instructions. Mature IL-1β levels of about 600-1500 pg/ml are observed for PBMCs in positive control wells.

The inhibitory potency of the compounds may be represented by an IC$_{50}$ value, which is the concentration of inhibitor at which 50% of the mature IL-1β is detected in the supernatant as compared to the positive controls.

Table 5 shows inhibition of IL-1β secretion from peripheral blood mononuclear cells for selected compounds of this invention as determined by the above methods.

Selected compounds have been tested in this assay and shown to inhibit IL-1β release with IC$_{50}$ values between 0.04 µM and 20 µM.

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 eg the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell based assay to screen compounds for inhibition of the caspase-8-mediated apoptotic pathway.

Experimental Procedure

Jurkat E6.1 cells are cultured in complete medium consisting of RPMI-1640 (Sigma No) +10% foetal calf serum (Gibco BRL No.10099-141) +2 mM L-glutamine (Sigma No. G-7513). The cells are harvested in log phase of growth. 100 ml of cells at $5-8 \times 10^5$ cells/ml are transferred to sterile 50 ml Falcon centrifuge tubes and centrifuged for 5 minutes at 100×g at room temperature. The supernatant is removed and the combined cell pellets resuspended in 25 ml of complete medium. The cells are counted and the density adjusted to $2 \times 10^6$ cells/ml with complete medium.

The test compound is dissolved in dimethyl sulfoxide (DMSO)(Sigma No. D-2650) to give a 100 mM stock solution. This is diluted to 400 µM in complete medium, then serially diluted in a 96-well plate prior to addition to the cell assay plate.

100 µl of the cell suspension ($2 \times 10^6$ cells) is added to each well of a sterile 96-well round-bottomed cluster plate (Costar No. 3790). 50 µl of compound solution at the appropriate dilution and 50 µl of anti-Fas antibody, clone CH-11 (Kamiya No. MC-060) at a final concentration of 10 ng/ml, are added to the wells. Control wells are set up minus antibody and minus compound but with a serial dilution of DMSO as vehicle control. The plates are incubated for 16-18 hrs at 37° C. in 5% $CO_2$ and 95% humidity.

Apoptosis of the cells is measured by the quantitation of DNA fragmentation using a 'Cell Death Detection Assay' from Boehringer-Mannheim, No. 1544 675. After incubation for 16-18 hrs the assay plates are centrifuged at 100×g at room temperature for 5 minutes. 150 µl of the supernatant are removed and replaced by 150 µl of fresh complete medium. The cells are then harvested and 200 µl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 µl of this solution is then assayed according to the manufacturer's instructions supplied with the kit. $OD_{405}$ nm is measured 20 minutes after addition of the final substrate in a SPECTRAmax Plus plate reader (Molecular Devices). OD405 nm is plotted versus compound concentration and the IC50 values for the compounds are calculated using the curve-fitting program SOFTmax Pro (Molecular Devices) using the four parameter fit option.

Selected compounds have been tested in this assay and shown to inhibit Fas-induced apoptosis of Jurkat cells with $IC_{50}$ values between 0.001 µM and 0.15 µM.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A compound of formula Ia:

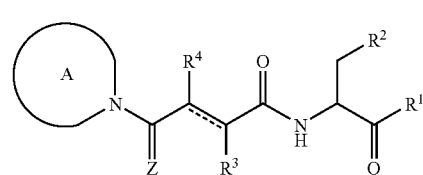

or a pharmaceutically-acceptable derivative thereof, wherein:

- - - - - next to $R^3$ represents a single or double bond;

Z is oxygen or sulfur;

$R^1$ is $CH_2Y$;

Y is an electronegative leaving group;

$R^2$ is $CO_2H$, $CH_2CO_2H$, or esters, amides or isosteres thereof;

$R^3$ is hydrogen, a side chain of a natural α-amino acid, or a substituted or unsubstituted group having a molecular weight up to about 140 Daltons selected from $C_{1-12}$ aliphatic, 5-14 membered aryl, (5-14 membered aryl)-($C_{1-12}$-alkyl)-, 3-9 membered heterocyclyl, or (3-9 membered heterocyclyl)-($C_{1-12}$-alkyl)-; wherein said $R^3$ is optionally substituted with halogen, —R, —OR, —OH, —SH, —SR, acyloxy, phenyl (Ph), —OPh, —$NO_2$, —CN, —$NH_2$, —NHR, —N(R)$_2$, —NHCOR, —NHCONHR, —NHCON(R)$_2$, —NRCOR, —$NHCO_2R$, —$CO_2R$, —$CO_2H$, —COR, —CONHR, —CON(R)$_2$, —S(O)$_2$R, —$SONH_2$, —S(O)R, —$SO_2NHR$, —NHS(O)$_2$R, =O, =S, =NNHR, =NNR$_2$, =N—OR, =NNHCOR, =$NNHCO_2R$, =$NNHSO_2R$, or =NR;

R is $C_{1-6}$ aliphatic;

$R^4$ is hydrogen or a $C_{1-6}$ aliphatic group that is optionally interrupted by —O—, —S—, —$SO_2$—, —CO—, —NH—, or —N($C_{1-4}$ alkyl)-, or $R^3$ and $R^4$ taken together with their intervening atoms optionally form a 3-7 membered ring having 0-2 heteroatoms selected from nitrogen, oxygen or sulfur;

Ring A is a nitrogen-containing mono-, bi- or tricyclic ring system having 0-5 additional ring heteroatoms selected from nitrogen, oxygen or sulfur provided that Ring A is not carbazole.

2. The compound of claim 1 wherein Z is oxygen and - - - - - next to $R^3$ represents a single bond.

3. The compound of claim 2 wherein $R^3$ is a $C_{1-4}$ alkyl group.

4. The compound of claim 3 wherein Ring A is selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

5. The compound of claim 4 wherein Ring A is selected from phenothiazine, β-carboline, pyrido[4,3-b]indole, 2,3,9-triazafluorene, 9-thia-2,10-diazaanthracene, 3,6,9-triazafluorene, phenoxazine, dibenzoazepine, dihydro-dibenzoazepine, dihydrophenazine, dihydroacridine, or dihydrophenanthridine.
6. The compound of claim 5 wherein Ring A is selected from phenothiazine or dihydrophenanthridine.
7. The compound of claim 1 wherein the compound is selected from the following Table 1 compounds:
Ia-12
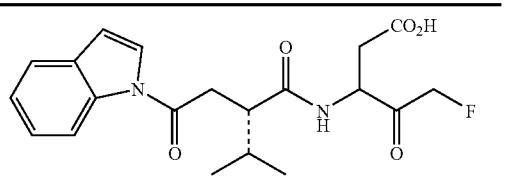
Ia-13
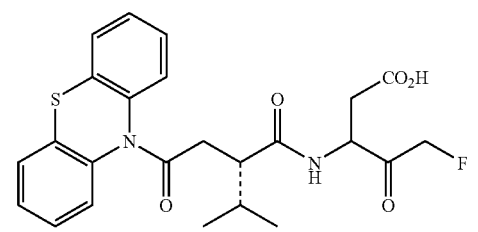
Ia-14
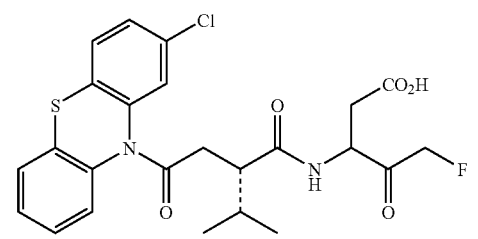
Ia-15
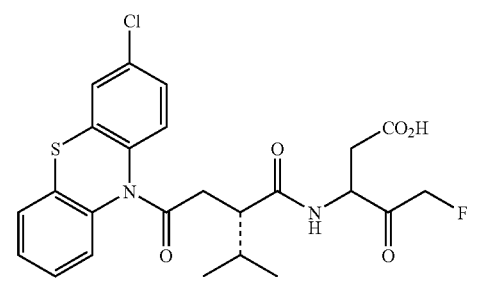
Ia-16
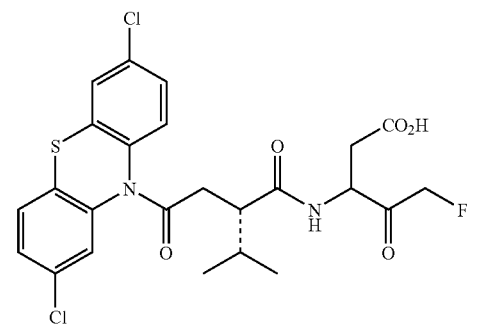
-continued
Ia-17
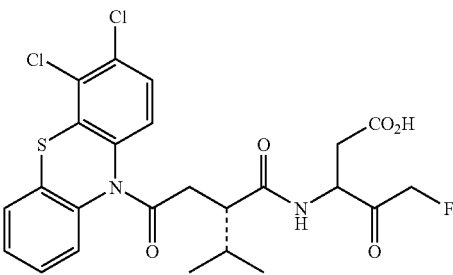
Ia-18
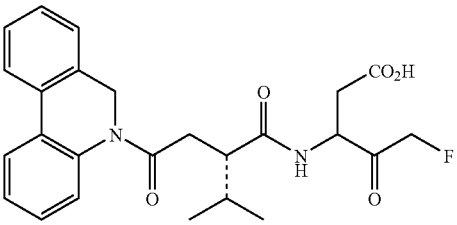
Ia-19
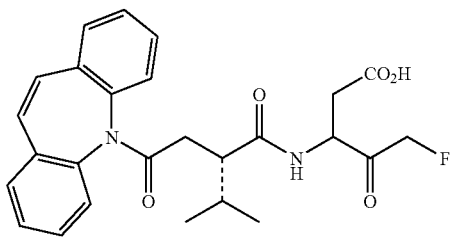
Ia-20
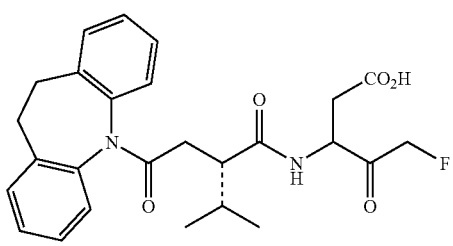
Ia-21
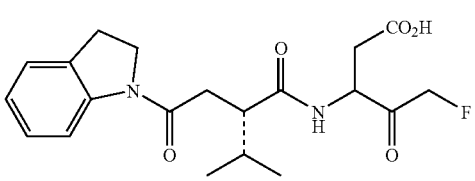
Ia-32
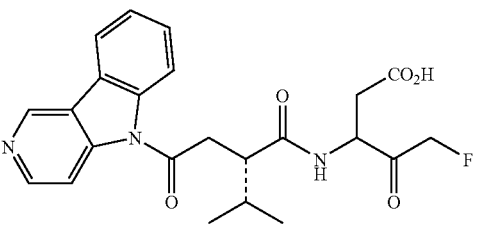

Ia-33 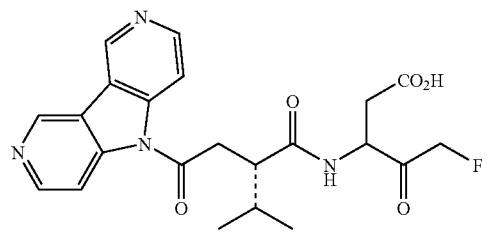
Ia-34 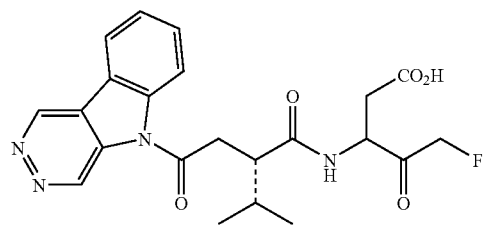
Ia-35 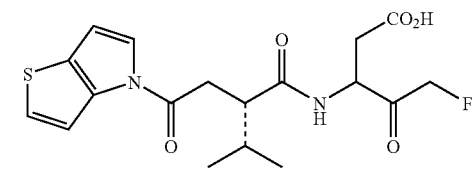
Ia-36 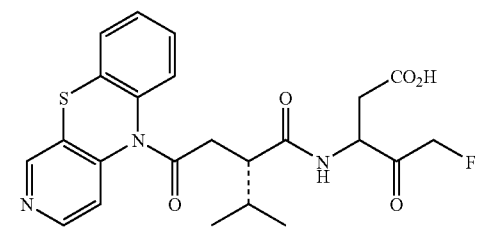
Ia-37 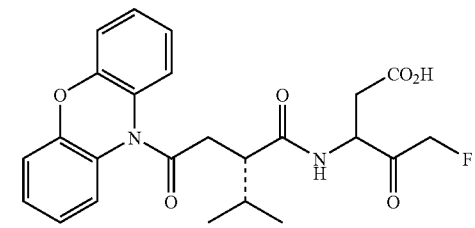
Ia-38 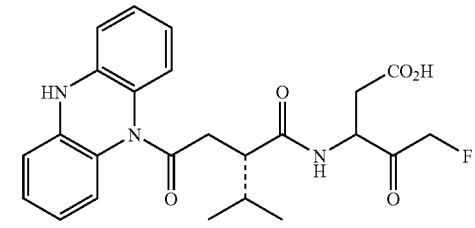
Ia-39 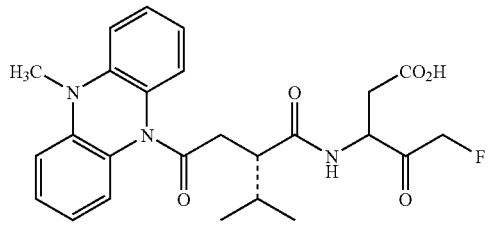
Ia-40 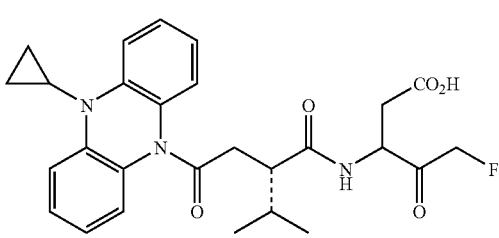
Ia-41 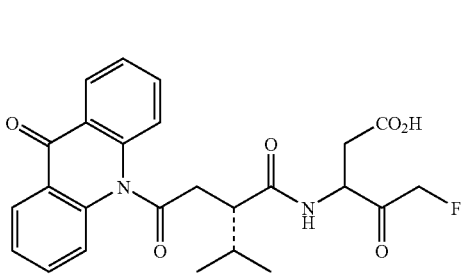
Ia-42 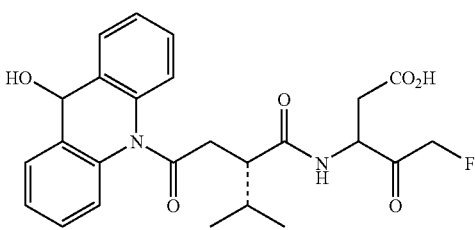
Ia-43 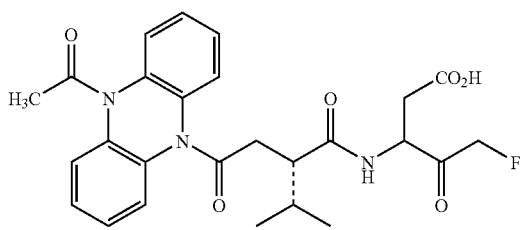
Ia-44 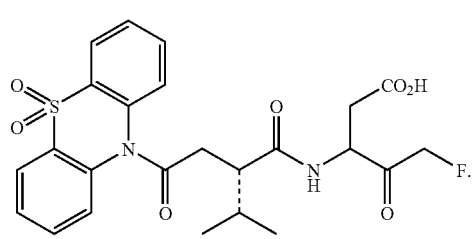
8. A pharmaceutical composition comprising a compound according to any one of claims 1-7 and a pharmaceutically acceptable carrier.
* * * * *